(12) United States Patent
Khorasani et al.

(10) Patent No.: US 8,145,001 B2
(45) Date of Patent: Mar. 27, 2012

(54) METHODS AND SYSTEMS FOR PROXY MEDICAL IMAGE COMPRESSION AND TRANSMISSION

(75) Inventors: Elahe Khorasani, Yorktown Heights, NY (US); Vadim Sheinin, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 847 days.

(21) Appl. No.: 12/243,226

(22) Filed: Oct. 1, 2008

(65) Prior Publication Data
US 2010/0080476 A1 Apr. 1, 2010

(51) Int. Cl.
  *G06K 9/36* (2006.01)
  *G06K 9/54* (2006.01)
(52) U.S. Cl. ........................ 382/232; 382/305
(58) Field of Classification Search .......... 382/232–251, 382/305; 709/203, 206, 227; 713/161, 168–170
See application file for complete search history.

(56) References Cited

U.S. PATENT DOCUMENTS

| | | | |
|---|---|---|---|
| 6,553,141 B1 | 4/2003 | Huffman | |
| 6,574,742 B1 * | 6/2003 | Jamroga et al. | 713/400 |
| 6,633,674 B1 | 10/2003 | Barnes et al. | |
| 7,216,173 B2 * | 5/2007 | Clayton et al. | 709/227 |
| 2004/0230613 A1 | 11/2004 | Goldstein et al. | |
| 2006/0122482 A1 | 6/2006 | Mariotti et al. | |
| 2007/0223793 A1 | 9/2007 | Gutman | |
| 2007/0237402 A1 | 10/2007 | Dekel et al. | |

FOREIGN PATENT DOCUMENTS

| | | |
|---|---|---|
| WO | 9928858 | 6/1999 |
| WO | 2004102949 | 11/2004 |

* cited by examiner

*Primary Examiner* — Ishrat I Sherali
(74) *Attorney, Agent, or Firm* — Tutunjian & Bitetto, P.C.; Brian P. Verminski, Esq.

(57) ABSTRACT

In accordance with one or more implementations of the present principles, digital medical images may be efficiently transmitted between industry protocol compliant stations. Proxies may be employed to intercept messages and data transmitted between the stations and to enable transmission of data between the stations in compressed form. Further, the proxies may be incorporated into existing systems without altering integrated components to permit efficient and seamless implementation of one or more compression schemes.

25 Claims, 7 Drawing Sheets

METHODS AND SYSTEMS FOR PROXY MEDICAL IMAGE COMPRESSION AND TRANSMISSION

BACKGROUND

1. Technical Field

The present principles generally relate to compression and transmission of images and, more particularly, to compression and transmission of industry protocol compliant images from a server to remote viewing stations.

2. Description of the Related Art

Industry protocol compliant images include digital medical images, which correspond to a class of data files that are relatively large in size and volume. A medical image volume may include multiple image "slices." Examples of digital medical images include magnetic resonance images (MRI), ultrasound (US) images, computed tomography (CT) images, typically referred to as "CAT scans," and positron emission tomography (PET) images, among others. Digital medical images are commonly stored, retrieved, transmitted and viewed in accordance with a standard format and communication protocol known as Digital Imaging Communications in Medicine (DICOM) in DICOM-enabled systems. DICOM is one example of an industry protocol.

DICOM images are stored in central repository servers referred to as Picture Archival and Communication Systems (PACS) servers. Remote Viewing Stations include DICOM-enabled applications that may query the PACS servers to retrieve the DICOM images for viewing. Current methods for viewing medical images entail using a DICOM enabled application to retrieve medical images from a PACS Server and to store and access them in a local storage medium. Modern medical images are rather large, utilizing up to 1 Gbyte of memory or more per file.

When a Viewing Station is connected to the PACS server via a high bandwidth local area network (LAN), downloading of the images is relatively quick and efficient. However, problems may arise when the Viewing Station is located in a remote facility and has a low-bandwidth connection to the PACS Server. For example, if the link between the PACS Server and the remote facility is in the range of 1 Mbit/sec, downloading medical images at the Viewing Station would be very slow and time consuming for medical professionals.

To overcome this problem, medical images may be compressed to reduce the size of the images for transmission. Known methods of compressing DICOM images fall into two main classes. Both classes require the inclusion of a compression engine in the PACS Server and a compatible decompression engine in the Viewer Application.

With reference to FIG. 1, the first class of methods, as illustrated in the block/flow diagram 100 in FIG. 1, entails storing the DICOM images in their original uncompressed form and compressing them in response to requests for the images from a remote viewer. In this method, a PACS Server 116 within a PACS Station 102 stores the DICOM images 115 in their original format in a DICOM database 105 using a DICOM enabled Server Application 106. The DICOM images 115 are received from a Medical Imaging Device 101, such as, for example MRI systems or CAT scan systems, through a high bandwidth LAN connection 114. When an image is requested from a remote Viewer Workstation 104, the PACS Server compresses the image by transmitting the compressed image 108 to an integrated encoder 107 for image compression and sends the compressed image 109 over a low bandwidth connection 103. A Viewer Application 110 utilizes an integrated decoder 112 that is compatible with the encoder 107 in the PACS server 116 to decode the images. The images may be displayed using a viewer 111 or they may be saved locally. An example of this class of methods is provided in U.S. Publication No. 2007/0237402, entitled "Adaptive Selection of Image Streaming Mode," to Dekel et al.

Referring to FIG. 2, the second main class of known methods for compressing DICOM images, as illustrated in block/flow diagram 200 of FIG. 2, includes employing a compression engine or encoder 215 and a DICOM Enabled Server Application 217 in a PACS server 202 within a PACS Station 203 to compress medical images prior to storing them. DICOM images 208 may be transmitted to PACS server 202 from a DICOM enabled medical imaging device 201 through a high bandwidth LAN 207. After compression, the PACS Server 202 stores the compressed images 209 in its database 216. Upon request from a remote Viewer workstation 205, the compressed images 210 may be sent along a low bandwidth connection 204 to a Viewer Application 212. Similar to the first class of methods, in these systems, the Viewer Application includes a viewer 213 and a compatible integrated decompression engine 214 to decode the images received from the PACS Server. An example of this class of methods is provided in U.S. Pat. No. 6,633,674, entitled "Picture Archiving and Communication System (PACS) Employing Improved Data Compression," to Barnes et al.

In both known classes the PACS Server Application and the Viewer Application are required to support compatible formats of compression. If one site does not support compression, or the supported formats of both sites are not compatible, using compression for reducing the transmission time of images is not possible. Thus in known methods, if a central FACS Server Application adds or upgrades its compression capabilities, existing Viewer Applications cannot take advantage of the improved capabilities unless they all implement compatible decompression schemes. These are major limitations, as they may not allow the various viewer application and PACS server applications with different levels of support to incorporate improved image compression.

Furthermore, applying known DICOM compression schemes in existing DICOM compatible systems that do not employ compression techniques requires considerable alteration of integrated components of the systems. Altering integrated components of existing DICOM compatible systems to include compression features entails significant verification routines to ensure that other components are minimally or inconsequentially affected. Thus, known methods of DICOM compression do not provide a seamless and efficient means for incorporating compression features within existing DICOM systems.

Accordingly, because of the shortcomings and limitations of known DICOM compression systems, there is a need for methods and systems that seamlessly enhance the efficiency of transferring large volumes of Medical Images to remote stations, without altering any existing PACS and viewer application software and user interfaces.

SUMMARY

Methods and systems in accordance with various implementations of the present principles address the deficiencies of the prior art by incorporating compression schemes within existing DICOM compatible systems without altering PACS server and viewer workstation software. In this way, for example, compression schemes may be efficiently integrated into existing DICOM systems while avoiding time consuming verification and correction routines. Moreover, according to aspects of the present principles, diagnostic quality of medical images may be maintained while significantly reducing the volume of data transmitted. Further, the manner in which users retrieve and view medical images in DICOM systems would not change in any way.

In one implementation of the present principles, a method for transmitting industry protocol compliant images from a server includes sending a request for image data to a Server Application from a Server Proxy emulating a Viewer Application, wherein the Server Application interprets the request as originating from the Viewer Application; intercepting a response to the request at the Server Proxy, wherein the response is generated at the Server Application and is directed to the Viewer Application; compressing the image data in response to an encoding command from the Server Proxy; and transmitting the compressed image data to a decoder.

In an alternate implementation of the present principles, a method for receiving industry protocol compliant images from a server includes intercepting a request for image data at a Viewer Proxy emulating a Server Application, wherein the request is generated at a Viewer Application and is directed to the Server Application; receiving compressed image data at a decoder and decompressing the compressed image data in response to a decoding command from the Viewer Proxy; and transmitting a response from the Viewer Proxy and the decompressed image data to the Viewer Application, wherein the Viewer Application interprets the response from the Viewer Proxy as originating from the Server Application.

In a different implementation of the present principles, a system for transmitting industry protocol compliant images from a server includes a Server Application configured to store image data at the server and service requests for the image data; a remote Viewer Application configured to transmit requests for the image data and to receive and read the image data; and a Server Proxy configured to send a request for the image data to the Server Application while emulating the Viewer Application, wherein the Server Application interprets the request as originating from the Viewer Application, intercept a response to the request, wherein the response is generated at the Server Application and is directed to the Viewer Application, and transmit compressed image data to a decoder; and an encoder configured to compress the image data in response to an encoding command from the Server Proxy.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of implementations of the present principles with reference to the following figures wherein.

DETAILED DESCRIPTION

According to one or more implementations of the present principles, two DICOM Enabled Proxy Applications may be added into the communication path of PACS Stations and Viewer Stations. These proxies may intercept communication data transmitted between a PACS Server and a Viewer Application in order to compress DICOM images on the PACS side and decompress them on the Viewer side. The proxies may be inserted in the path of any existing PACS Server and DICOM Viewer without altering them. In addition, predictive compression algorithms, such as, for example, H.264, among others, may be employed to achieve high compression ratios while maintaining diagnostic quality. However, it should be understood that any compression algorithms may be utilized in various implementations of the present principles.

Furthermore, it should also be understood that the terms "image," "image data," and/or "image information," as employed herein, may correspond to stand alone images or video images or streams with or without audio components. Thus, one of ordinary skill in the art, based on the teachings of this disclosure, may straightforwardly apply the teachings disclosed herein to all such types of data. Moreover, although DICOM Compliant systems are described as exemplary implementations of the present principles, aspects of the present principles may be applied by one of skill in the art in systems employing other industry protocols.

Figure 1:
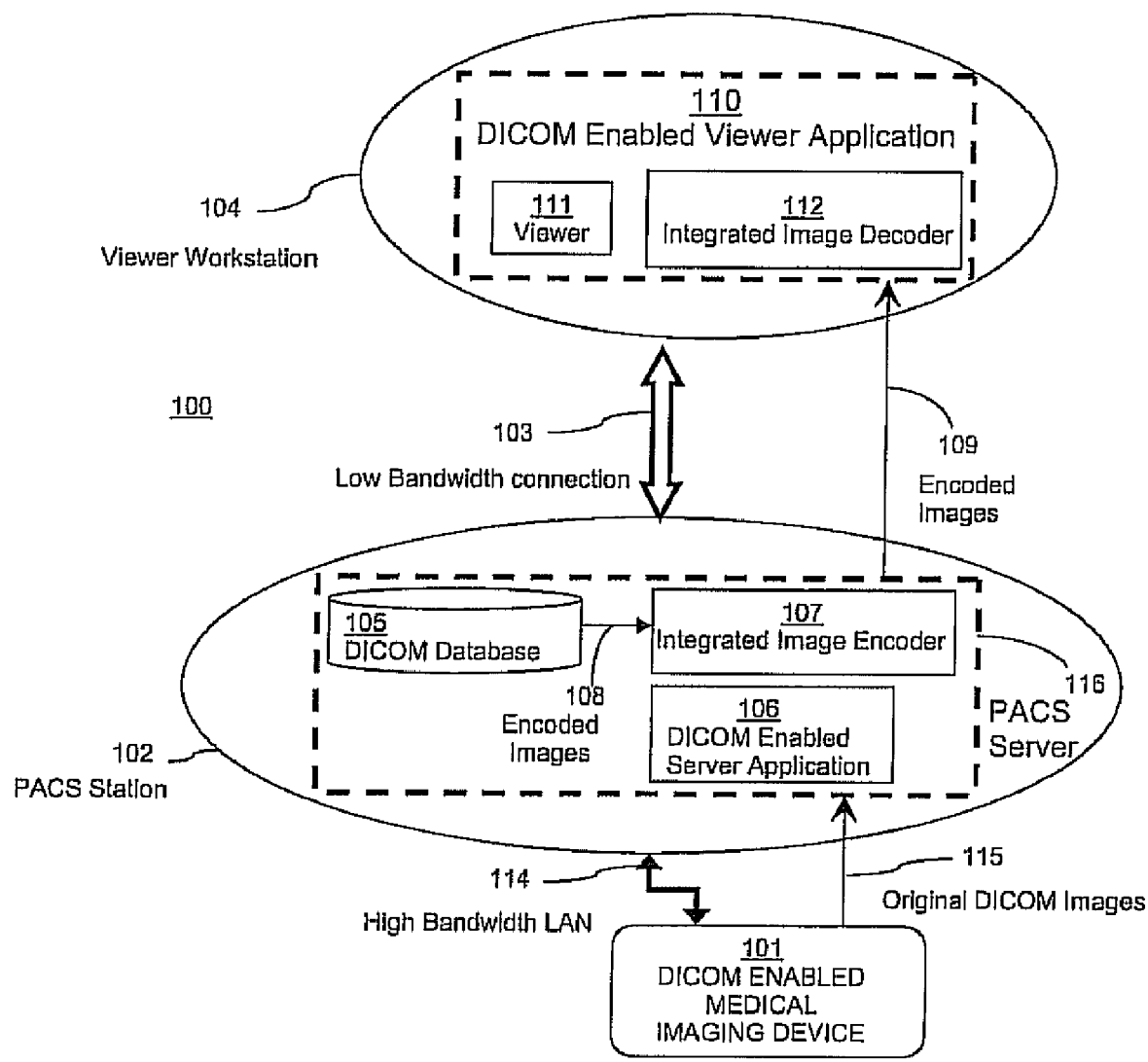
FIG. 1 is a high level block/flow diagram illustrating a first class of prior art DICOM compression architectures.
Figure 2:
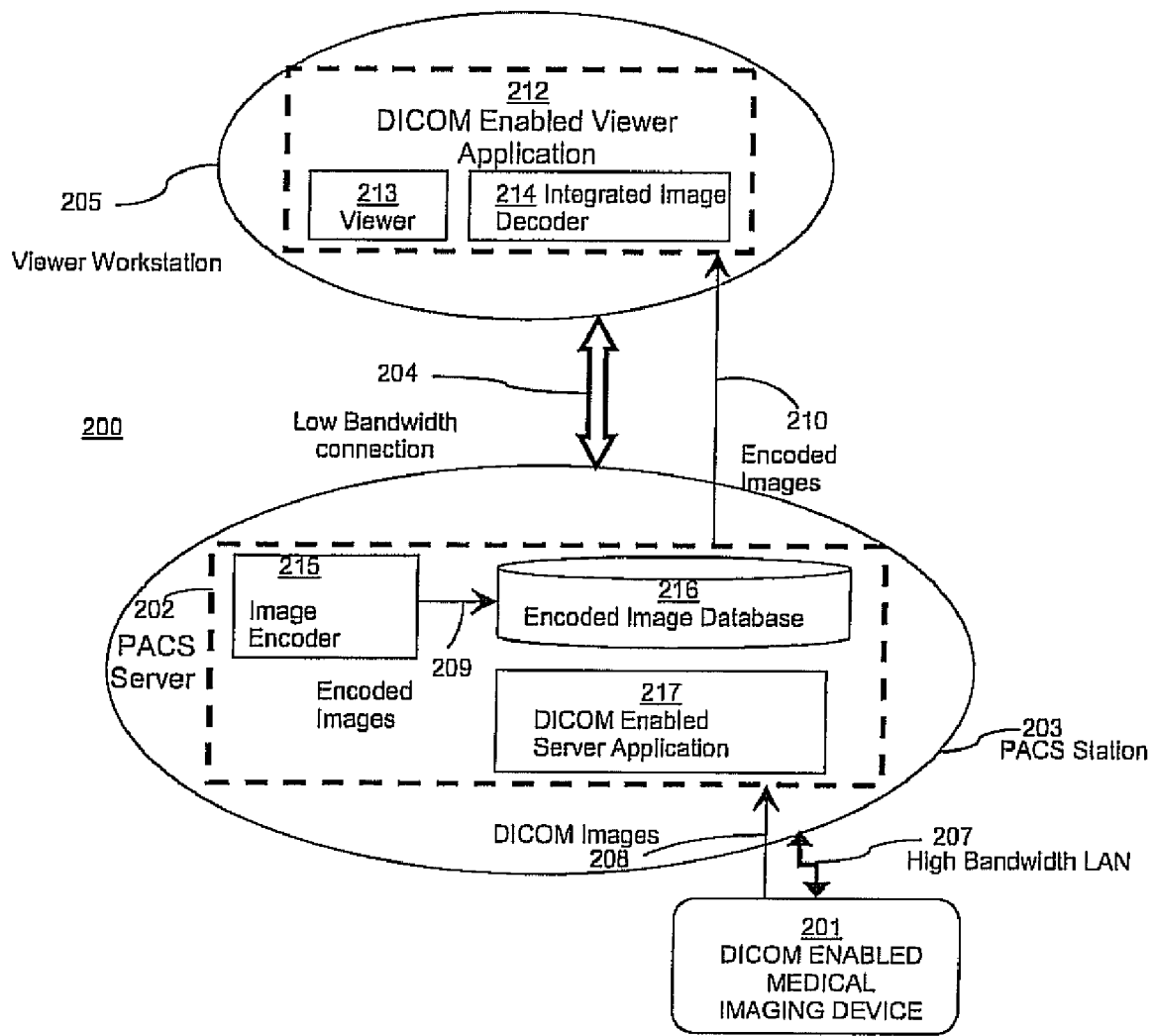
FIG. 2 is a high level block/flow diagram illustrating a second class of prior art DICOM compression architectures.
Figure 3:
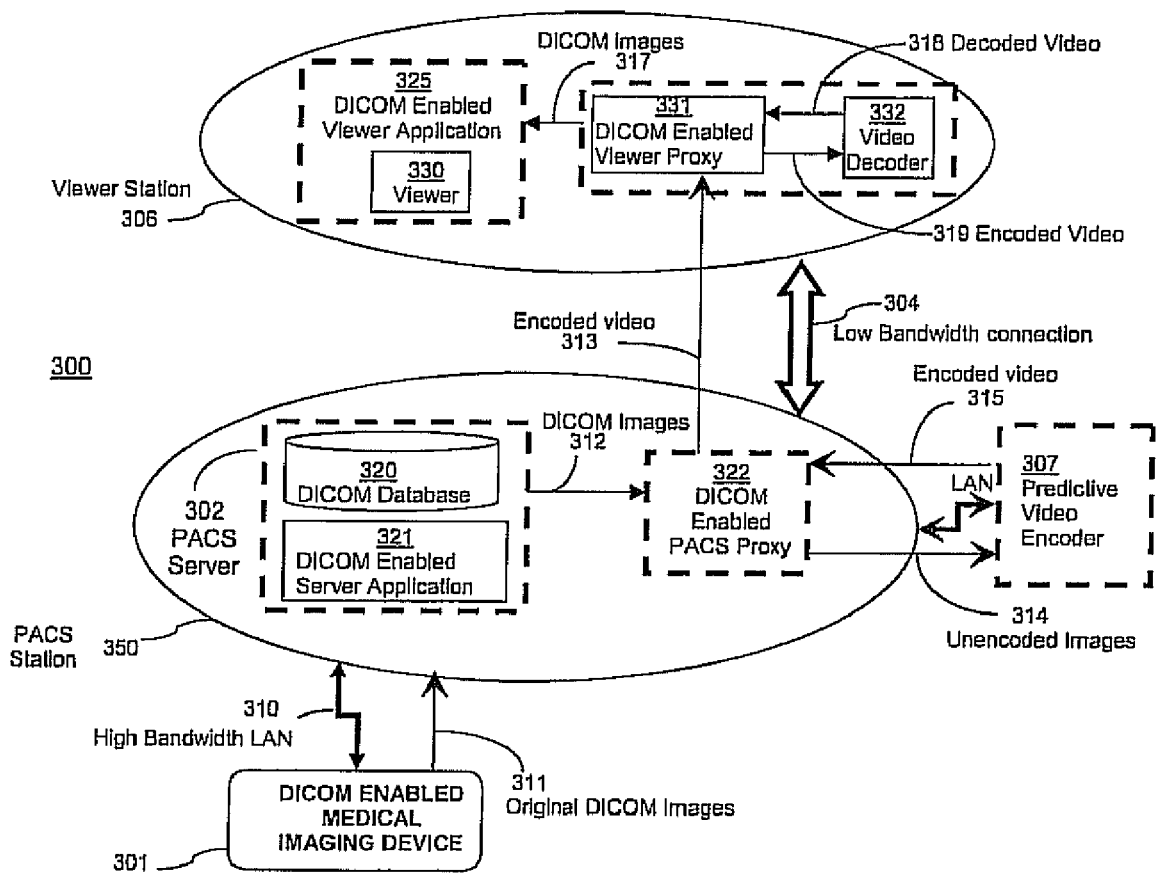
FIG. 3 is a high level block/flow diagram illustrating a system in accordance with one implementation of the present principles in which proxies may be employed to seamlessly and efficiently incorporate a compression scheme in industry protocol compliant systems.

Referring now in detail to the figures in which like numerals represent the same or similar elements and initially to FIG. 3, one implementation of a system 300 according to aspects of the present principles is illustrated. The system may include a PACS Station 350 and a remote Viewer Station 306 that are linked through a relatively low-bandwidth connection 304, which may be the internet, for example. The PACS Station 350 may include a PACS Server 302 comprising a DICOM Database 320 and a DICOM or PACS Server Application 321 that controls the server 302 and the database 320. The DICOM database 320 may have stored thereon DICOM-compliant medical images, such as, for example, CT images, CAT Scan images, and MRI images, as discussed above. Further, the PACS Station 102 may be linked to a DICOM enabled medical imaging device 301, such as, for example, MRI Systems and CT systems, as discussed above, from which original, large DICOM images 311 may be transmitted along a high bandwidth local area network link 310 for storage in the database 320.

The Viewer Station 306 may include a DICOM enabled Viewer Application 325 that may employ protocols to request and retrieve DICOM images from a PACS server. In addition, the DICOM images may be viewed on viewer 330. While a single Viewer Station is depicted in FIG. 3, it should be understood that many Viewer Stations may be included in system 300 and may communicate with PACS Server 302 to obtain digital medical images.

According to one or more aspects of the present principles, as illustrated in FIG. 3, a DICOM enabled PACS Proxy 322 may be incorporated in the PACS station 350 and a DICOM Viewer Proxy 331 may be incorporated in the Viewer Station 306. A PACS Proxy is one example of a "Server Proxy" and a DICOM Viewer Proxy is one example of a "Viewer Proxy," as the terms are applied herein. The PACS Proxy 322 and the DICOM Viewer Proxy 331 may control encoder 307 and decoder 332, respectively.

Further, the two proxies 322 and 331 may be full DICOM engines that perform all DICOM services, such that they communicate with the PACS Server Application 321 and Viewer Application 325 as if they were the actual target DICOM station. Thus, a "Viewer Proxy," as the term is defined herein, uses protocols employed by a Viewer Application to communicate with the Viewer Application as if it were a Server Application. In this way, the Viewer Proxy emulates the Server Application and the Viewer Application interprets communication from the viewer Proxy as originating from the Server Application. Similarly, the "Server Proxy," as the term is defined herein, uses protocols employed by a Server Application to communicate with the Server Application as if it were the Viewer Application. As such, in this manner, the Server Proxy emulates the Viewer Application and the Server Application interprets communication from the Server Proxy as originating from the Viewer Application.

PACS Proxy 322 may receive a DICOM image file 312 at the PACS station and transmit the unencoded images along line 314 to a Predictive Video Encoder 307. In response to encoding or compression commands issued by the PACS Proxy 322, the encoder 307 may compress the file's image slices into an encoded video stream 315, which may be transmitted to the Viewer Station 306 over connection 304. The encoded or compressed video stream 315 may be received by Viewer Proxy 331 along line 313 and may be transmitted to a video decoder 332 along line 319. The video stream may be decompressed or decoded by the decoder 332 in response to decompression or decoding commands issued by the Viewer Proxy 331 and transmitted to the Viewer Proxy 331 along line 318. Additionally, the video stream may be converted to a DICOM file that may be sent along line 317 to the Viewer Application 325. In this implementation, the PACS Server Application and Viewer Application, as well as the user interface for downloading the images, are unaltered.

It should be noted that according to aspects of the present principles, video compression schemes for large volumes of data that has a high correlation between successive frames, similar to CT images, for example, may be used as opposed to schemes that compress individual slices independently from each other. Experiments conducted by the Applicants, have shown that lossy video compression standards, such as, for example, H.264, with a compression ratio of more than 10:1 may preserve the diagnostic quality of such images. A compression ratio of 10:1 or more, for example, may substantially reduce transmission time between PACS Servers and remote viewer stations accessed by medical professionals. In addition, it should also be noted that due to the confidential nature of the images, encryption schemes may be applied as is known in the art for storing and/or transmitting medical images in or between PACS Stations and Viewer Stations.

With respect to DICOM-compliant implementations of the present principles, configuration tables of applications may be modified to permit communication between the Viewer and Server Proxies and DICOM applications. For example, the application title of the Viewer Proxy may be added to the configuration table of the DICOM Viewer Application and the application title of the Server Application may be added to the PACS Server Application configuration table.

Further, it should also be understood that in one implementation, elements 302, 320, 321, 322 and 307 may be implemented in a single computer readable medium and elements 325, 331 and 332 may be implemented in another computer readable medium. Moreover, method steps described herein may be embodied on one or more of such computer readable mediums in the form of program instructions executable by a computer to perform method steps described herein.

Figure 4:
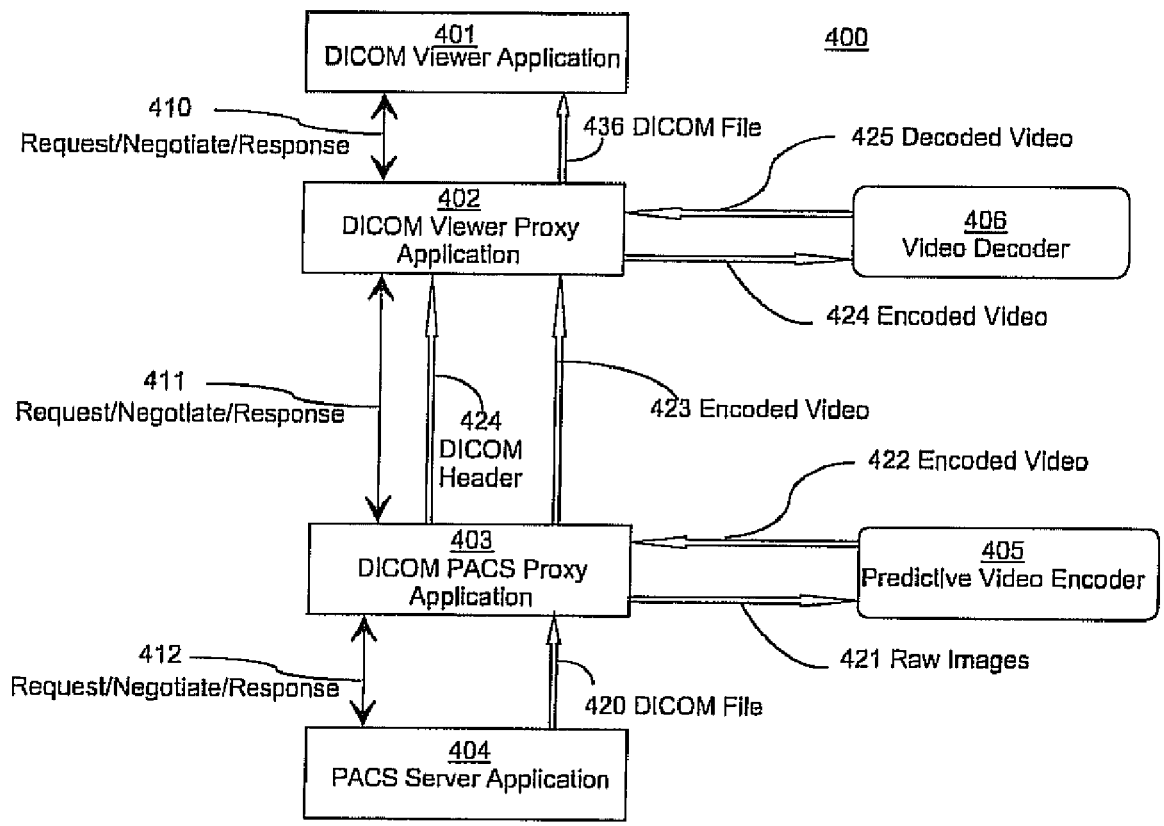
FIG. 4 is a high level block/flow diagram illustrating information flow in a more specific implementation of the system depicted in FIG. 3.
Figure 5:
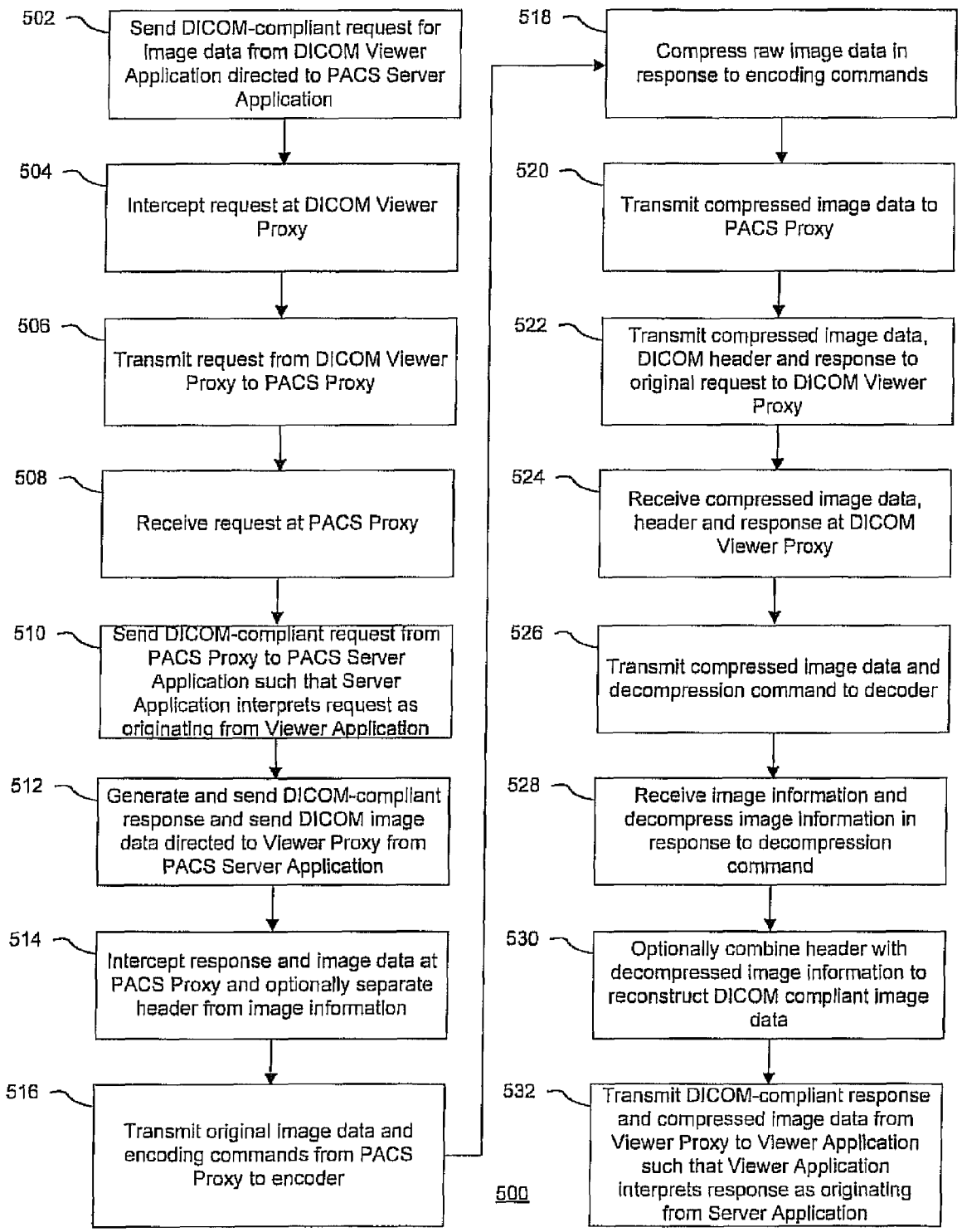
FIG. 5 is a high level flow diagram illustrating a method implementation in accordance with aspects of the present principles for incorporating a compression scheme in industry protocol compliant systems.

With reference to FIGS. 4 and 5, method implementations for transmitting and receiving industry protocol compliant images from a server according to aspects of the present principles are illustrated. Specifically, FIG. 4 depicts a high-level block/flow diagram 400 illustrating system components described above with respect to FIG. 3 and FIG. 5 depicts a high-level flow diagram of a method implementation 500. As illustrated in FIG. 4, system components may include a DICOM Viewer Application 401, a DICOM Viewer Proxy 402, a video decoder 406, a DICOM PACS Proxy 403, a PACS Server Application 404 and a Predictive Video Encoder 405, which may correspond to the similarly named system components discussed above with respect to FIG. 3. The DICOM Viewer Proxy 402 and the PACS Proxy 403 may be implemented in software applications.

Referring to FIG. 5 with continuing reference to FIG. 4, a DICOM Viewer Application 401 may send a DICOM-compliant request along line 410 for image data in the form of a DICOM file at step 502. Here, DICOM Viewer Application 401 may address and/or direct the request to PACS Server Application 404.

At step 504, the DICOM Viewer Proxy 402 may intercept and/or evaluate the request. In addition, the DICOM Viewer Proxy 402 may negotiate the transfer syntax with the Viewer Application 401 along line 410.

At step 506, the DICOM Viewer Proxy 402 may transmit the request to the PACS Proxy 403 along line 411. In some implementations, the request may be altered prior to transmission to the PACS proxy.

At step 508, the PACS Proxy 403 may receive the request along line 411 and may evaluate the request. It should be noted that in some implementations, that the PACS Proxy may intercept the request and receive it directly from the DICOM Viewer Application 401 so that the DICOM Viewer Proxy is bypassed.

At step 510, the PACS Proxy 403 may negotiate the transfer syntax with the PACS Server Application 404 and may send the request in a DICOM-compliant format along line 412. As stated above, the request is for the retrieval of image data. The PACS Server Application 404 may interpret the request as directly originating from DICOM Viewer Application 401 without any awareness of the PACS Proxy 403 and/or the DICOM Viewer Proxy 402. Further, in some implementations, the PACS Server Application 404 may receive the request directly from the DICOM Viewer Proxy 402, bypassing the PACS Proxy 403.

At step 512 the PACS Server Application 404 may acknowledge the request by generating and sending a DICOM-compliant response along line 412 after receiving and evaluating the request. Additionally, the PACS Server Application 404 may send image data in the form of a DICOM file along line 420. Here, the response and/or the DICOM file may be addressed and/or directed to DICOM Viewer Application 401.

At step 514, the PACS Proxy may intercept and evaluate the response and the image data.

As stated above, the image data may be in the form of one or more DICOM files, which are composed of two sections, header and image information. The header may include patient information, the type of scan, and other image information as well as file format and transfer syntax. The image or pixel information includes a number of individual image slices that may be stacked to form a three-dimensional volume. In accordance with an implementation of the present principles, compressing and decompressing a DICOM file may entail separating the image information from the header before compression and combining them back together after decompression. Further, in some implementations, a DICOM header should not be compressed and should be transferred as is to preserve its precise format, structure and data.

Thus, after or in response to receiving image data from the PACS Server Application 404, PACS Proxy 403 may parse the header for any of the above-recited information and separate the header from image data at step 514. As stated above, the image data may be composed of image slices.

At step 516, PACS Proxy 403 may send raw image data, encoding commands and/or parsed header information to video encoder 405 along line 421.

At step 518, encoder 405 may compress the raw image data in response to encoding or compression commands sent from PACS Proxy 403. Additionally, the encoder 405 may employ the parsed information to compress the image information.

At step 520, the compressed image data may be transmitted from the encoder 405 to the PACS Proxy 403 along line 422.

At step 522 the PACS Proxy 403 may transmit the compressed image data, the image header and the response to the original request to the DICOM Viewer Proxy 402 along lines 423, 424 and 411, respectively. Although the image header and the response are described here as being transmitted to the Viewer Proxy 402 simultaneously with the compressed image information, either or both the DICOM header and/or the response may be sent before or after the compressed image information is sent. Thus, the header, compressed image information and the response may be sent to the DICOM Viewer Proxy in any order. Further, in some implementations, the response may be sent directly to the Viewer Application 401 from the PACS Proxy 403.

At step 524, the DICOM Viewer Proxy 402 may receive the header, the response and the compressed image information.

At step 526, the DICOM Viewer Proxy 402 may send the compressed image information to video decoder 406 and may send a command to decode or decompress the compressed image information to video decoder 406 along line 424.

At step 528, the video decoder 406 receives the compressed image information and, in response to receiving a command to decode or decompress the image information, the video decoder 406 may decompress the image information and transmit the decompressed information to the DICOM Viewer Proxy 402 along line 425.

At step 530, the DICOM Viewer Proxy may 402 may combine the DICOM header with the decompressed image information to reconstruct DICOM-compliant image data.

At step 532, the DICOM Viewer Proxy may transmit a DICOM-compliant response to the original request generated by the DICOM Viewer Application 401, discussed above, to the DICOM Viewer Application 401 along line 410. As discussed above, the DICOM Viewer Proxy 401 may emulate the PACS Server Application 404 such that the DICOM Viewer Application 401 interprets the response as originating directly from the PACS Server Application 404. In addition, the DICOM-compliant data or image data may be transmitted to the DICOM Viewer Application 401 along line 436. The DICOM data may be transmitted in the form of one or more DICOM files.

It should be understood that modifications to implementations of the present principles described above may be made to those of ordinary skill in the art. For example, such an implementation is illustrated in the flow diagram of FIGS. 6 and 7, depicting an alternate system and method in accordance with aspects of the present principles.

Figure 6:
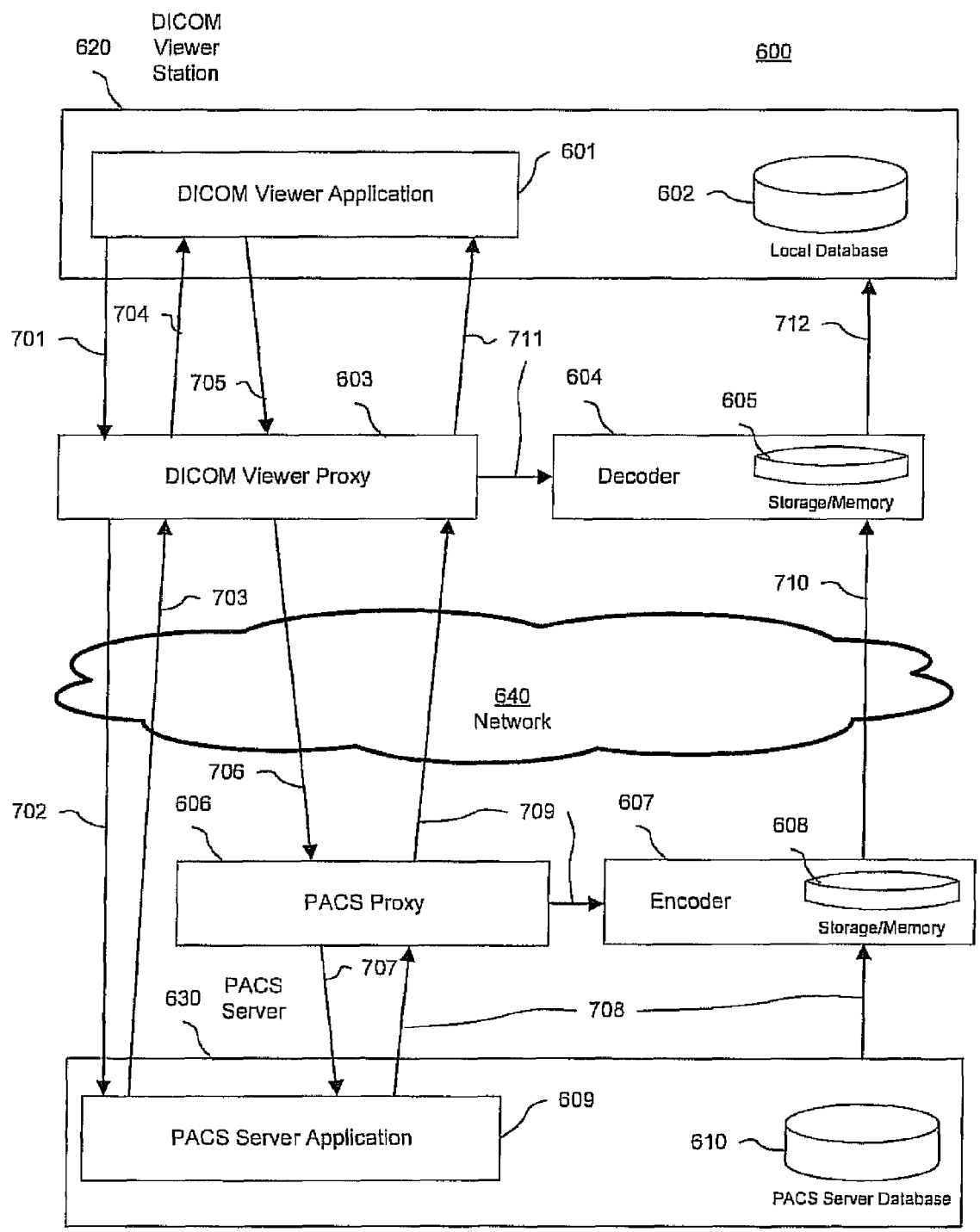
FIG. 6 is a high level block/flow diagram illustrating information flow of an alternative system implementation of the present principles.
Figure 7:
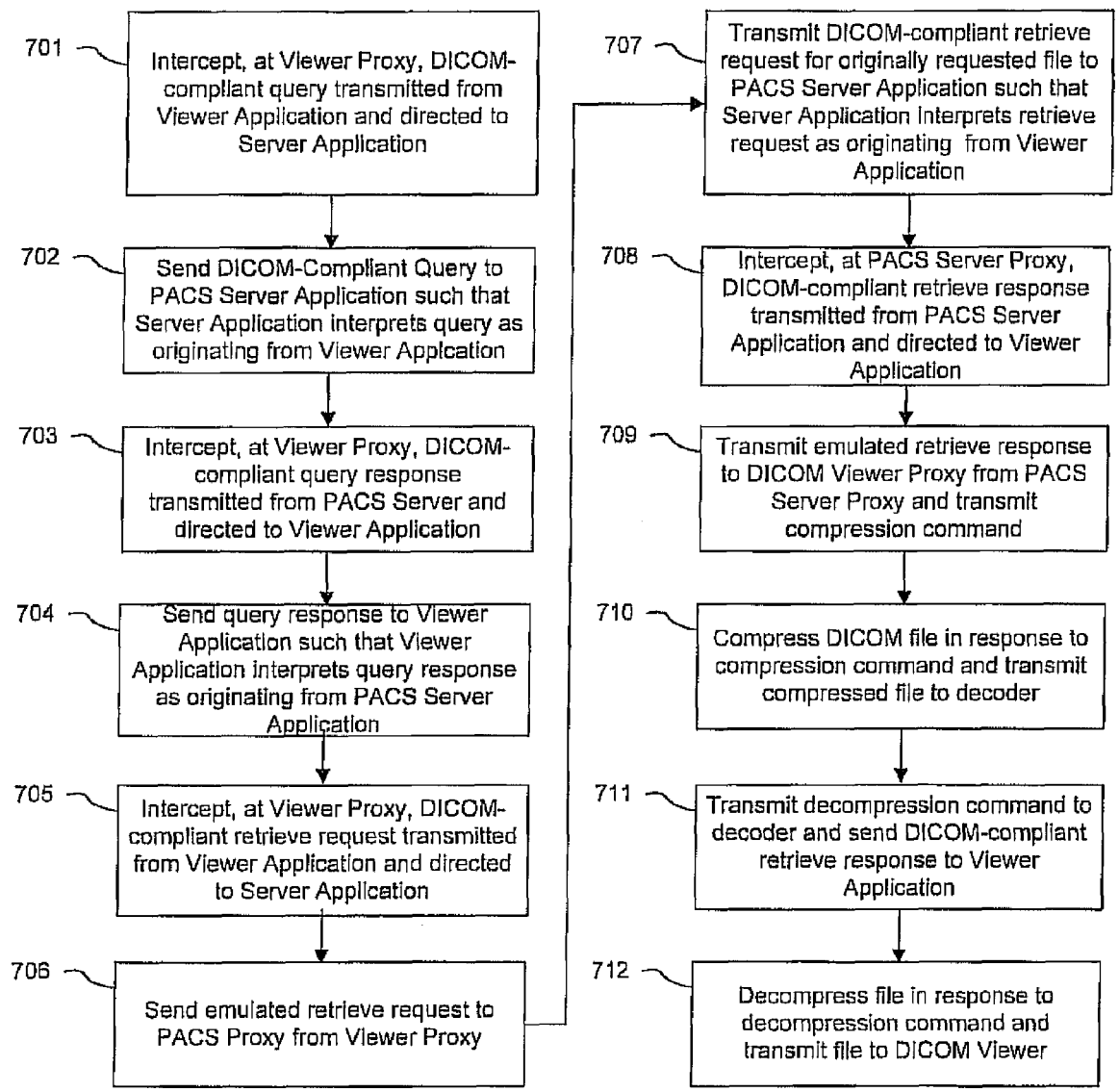
FIG. 7 is a high level flow diagram illustrating another method implementation in accordance with aspects of the present principles for incorporating a compression scheme in industry protocol compliant systems.

With reference to FIG. 6 and FIG. 7, another system and method implementation for transmitting and receiving DICOM compliant images from a PACS server is shown. A system 600 in accordance with aspects of the present principles may include DICOM Viewer Application 601, a local Viewer database 602, a DICOM Viewer Proxy 603, a decoder 604 including storage/memory 605, a PACS Proxy 606, an encoder 607 including storage/memory 608, a PACS Server Application 609 and a PACS Server Database 610. DICOM Viewer Application 601 and local viewer database 602 may be implemented in a Viewer Station 620. Additionally, PACS Server Application 609 and database 610 may be implemented in a PACS Server 630. Moreover, communications between DICOM Viewer Proxy 603, Decoder 604, PACS Proxy 606 and Encoder 607 may be conducted on network 640, which may, for example, be comprised of the internet, a local area network, a wide area network, etc.

In accordance with aspects of the present principles, method 700 may begin at step 701 in which the Viewer Proxy 603 intercepts a DICOM-compliant query transmitted from DICOM Viewer Application 601 and directed and/or addressed to the PACS Server Application 609. The query may be made to determine whether a DICOM file, which may comprise image or video data, is available at PACS Server 630. In addition, the DICOM Viewer Proxy 603 may evaluate the query after intercepting it.

At step 702, the DICOM Viewer Proxy 603 may send the DICOM-compliant query to the PACS Server Application 609. The PACS Server Application 609 may interpret the query as originating directly from Viewer Application 601.

At step 703, the DICOM Viewer Proxy 603 may intercept a DICOM-compliant query response transmitted from the PACS Server Application 609 and directed and/or addressed to DICOM Viewer Application 601. The query response may indicate whether the requested DICOM file is available or is located at the PACS Server 630. In addition, the DICOM Viewer Proxy 603 may evaluate the query after intercepting it.

At step 704, the DICOM Viewer Proxy 603 may send the query response to the DICOM Viewer Application 601. Viewer Application 601 may interpret the query response as originating from PACS Server Application 609.

At step 705, DICOM Viewer Proxy 603 may intercept a retrieve request transmitted from DICOM Viewer Application 601 and directed and/or addressed to the PACS Server Application 609. The retrieve request may be made to retrieve the requested DICOM file. In addition, the DICOM Viewer Proxy 603 may evaluate the query after intercepting it.

At step 706, the DICOM Viewer Proxy 603 may send an emulated retrieve request to the PACS Proxy 606. The format of the retrieve request may be DICOM compliant or may be in accordance with another protocol. The alternative protocol may be any communication protocol compatible with the network on which the message is transmitted, such as a local area network, a wide area network or the internet. Further, the protocol may be chosen such that the message is transmitted in a relatively faster or more efficient manner as compared to a DICOM-compliant message.

At step 707, the PACS Proxy 606 may transmit a DICOM-compliant retrieve request for the originally requested DICOM File to the PACS Server Application 609. The PACS Server Application 609 may interpret the retrieve request as originating from Viewer Application 601.

At step 708, the PACS Proxy 606 may intercept a DICOM-compliant retrieve response transmitted from the PACS Server Application 609 and directed and/or addressed to DICOM Viewer Application 601. The retrieve response may indicate that the requested file is or will be transmitted. In addition, the DICOM Viewer Proxy 603 may evaluate the query after intercepting it. Further, an uncompressed DICOM file transmitted from the PACS Server 630 and directed and/or addressed to the DICOM Viewer Application 601 may be intercepted by DICOM Viewer Proxy 603 or encoder 607 and stored in memory 608.

At step 709, the PACS Proxy 606 may transmit an emulated retrieve response to the DICOM Viewer Proxy 603. The format of the emulated retrieve response may be DICOM compliant or in accordance with an alternative protocol, as discussed above. Additionally, the PACS Proxy 606 may transmit a compression command to the encoder 607.

At step 710, the encoder 607, in response to the command transmitted from the PACS Proxy 606, may compress the DICOM file and transmit the compressed file to DICOM Viewer Proxy 603 or decoder 604. The compressed file may be stored in memory 605.

At step 711, the DICOM viewer proxy 603 may transmit a decompression or decoding command to decoder 604. In addition, the DICOM Viewer Proxy 603 may send a DICOM-compliant retrieve response to DICOM Viewer Application 601, indicating that the originally requested DICOM file is being or will be transmitted. Viewer Application 601 may interpret the retrieve response as originating from PACS Server Application 609.

At step 712, the decoder 604 may decompress the file. Further, the decompressed file may be transmitted in accordance with DICOM to the DICOM Viewer Station 620 for storage in local viewer database 602. Similar to the retrieve response, Viewer Application 601 may interpret the decompressed file as originating directly from PACS Server. Application 609.

In implementations of the present principles, the DICOM Viewer Proxy behaves as if it is the PACS Server Application to the DICOM Viewer Application, and the PACS Proxy behaves as if it were the DICOM Viewer Application to the PACS Server Application. As a result, neither the Viewer Application nor the PACS Server Application has to be altered to enable them to communicate with the proxies and to utilize compression schemes in the transfer of DICOM data. Thus, in accordance with aspects of the present principles, incorporation of compression schemes into existing DICOM systems may be achieved without incurring the cost associated with significant verification testing and correction schemes that would otherwise be required for integrated compression and decompression schemes employed in known methods discussed above.

It should be understood that the elements shown in FIGS. 3-7 may be implemented in various forms of hardware, software or combinations thereof. Preferably, these elements are implemented in software on one or more appropriately programmed general-purpose digital computers having a processor and memory and input/output interfaces.

Implementations of the present principles can take the form of an entirely hardware embodiment, an entirely software embodiment or an embodiment including both hardware and software elements. In a preferred embodiment, the present invention is implemented in software, which includes but is not limited to firmware, resident software, microcode, etc.

Moreover, the implementations of the present principles can take the form of a computer program product accessible from a computer-usable or computer-readable medium providing program code for use by or in connection with a computer or any instruction execution system. For the purposes of this description, a computer-usable or computer readable medium can be any apparatus that may include, store, communicate, propagate, or transport the program for use by or in connection with the instruction execution system, apparatus, or device. The medium can be an electronic, magnetic, optical, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope and spirit of the invention as outlined by the appended claims. Having thus described aspects of the invention, with the details and particularity required by the patent laws, what is claimed and desired protected by Letters Patent is set forth in the appended claims.

What is claimed is:

1. A method for transmitting industry protocol compliant images from a server comprising:

sending a request for image data to a Server Application from a Server Proxy emulating a Viewer Application, wherein the Server Application interprets the request as originating from the Viewer Application;

intercepting a response to the request at the Server Proxy, wherein the response is generated at the Server Application and is directed to the Viewer Application;

compressing the image data in response to an encoding command from the Server Proxy; and transmitting the compressed image data.

2. The method of claim 1, wherein the Server Application is a Picture Archival and Communication Systems (PACS) Server Application, the Viewer Application is a Digital Imaging Communications in Medicine (DICOM) Viewer Application, the Server Proxy is a PACS Proxy and the request is DICOM compliant.

3. The method of claim 2, further comprising:

separating a DICOM header from image information at the PACS Proxy prior to compressing the image information.

4. The method of claim 1, wherein the image data is transmitted to a decoder controlled by a Viewer Proxy that emulates the Server Application.

5. The method of claim 4, further comprising the steps of:
decompressing the image data at said decoder;
transmitting the decompressed image data to the Viewer Application; and
sending a second response to the Viewer Application from the Viewer Proxy, wherein the Viewer Application interprets the second response from the Viewer Proxy as originating from the Server Application.

6. The method of claim 5, further comprising:
reconstructing the image data by combining a Digital Imaging Communications in Medicine (DICOM) header with decompressed image information.

7. The method of claim 1, wherein the compressing is performed in accordance with a lossy compression scheme.

8. The method of claim 7, wherein the compressing is performed in accordance with an H.264 compression standard.

9. A non-transitory computer readable medium tangibly embodying a program of instructions executable by a computer to perform the method steps recited in claim 1.

10. A method for receiving industry protocol compliant images from a server comprising:
intercepting a request for image data at a Viewer Proxy emulating a Server Application, wherein the request is generated at a Viewer Application and is directed to the Server Application;
receiving compressed image data and decompressing the compressed image data in response to a decoding command from the Viewer Proxy; and
transmitting a response from the Viewer Proxy and the decompressed image data to the Viewer Application, wherein the Viewer Application interprets the response from the Viewer Proxy as originating from the Server Application.

11. The method of claim 10, wherein the Server Application is a Picture Archival and Communication Systems (PACS) Server Application, the Viewer Application is a Digital Imaging Communications in Medicine (DICOM) Viewer Application, the Viewer Proxy is a DICOM Viewer Proxy and the request and decompressed image data are DICOM compliant.

12. The method of claim 11, further comprising:
separating a DICOM header from image information at a PACS proxy prior to compressing the image information.

13. The method of claim 10, further comprising:
sending a second request for the image data from a Server Proxy emulating a Viewer Application to a Server Application, wherein the Server Application interprets the second request as originating from the Viewer Application.

14. The method of claim 10, further comprising:
reconstructing the image data by combining a Digital Imaging Communications in Medicine (DICOM) header with decompressed image information.

15. The method of claim 10, wherein the compressed image data is compressed with an encoder that is controlled by a Server Proxy emulating the Viewer Application.

16. The method of claim 15, wherein the compressed image data is compressed in accordance with a lossy compression scheme.

17. The method of claim 16, wherein the compressed image data is compressed in accordance with an H.264 compression standard.

18. A non-transitory computer readable medium tangibly embodying a program of instructions executable by a computer to perform the method steps recited in claim 10.

19. A system for transmitting industry protocol compliant images from a server comprising:
a Server Application configured to store image data at the server and service requests for the image data;
a remote Viewer Application configured to transmit requests for the image data and to receive and read the image data; and
a Server Proxy configured to
send a request for the image data to the Server Application while emulating the Viewer Application, wherein the Server Application interprets the request as originating from the Viewer Application,
intercept a response to the request, wherein the response is generated at the Server Application and is directed to the Viewer Application, and
transmit compressed image data; and
an encoder configured to compress the image data in response to an encoding command from the Server Proxy.

20. The system of claim 19, further comprising:
a Viewer Proxy configured to
intercept a second request for image data, wherein the second request is generated at the Viewer Application and is directed to the Server Application,
transmit a second response to the second request and decompressed image data to the Viewer Application while emulating the Server Application, wherein the Viewer Application interprets the second response as originating from the Server Application, and
control a decoder such that the decoder decompresses the image data in response to a decoding command from the Viewer Proxy.

21. The system of claim 20, wherein the image data stored in the server, the request, the response and the decompressed image data are compliant with the industry protocol.

22. The system of claim 20, wherein the Server Application is a Picture Archival and Communication Systems (PACS) Server Application, the Server Proxy is a PACS proxy, the Viewer Application is a Digital Imaging Communications in Medicine (DICOM) Viewer Application, the Viewer Proxy is a DICOM Viewer Proxy, and the image data stored in the server, the request, the response and the decompressed image data are DICOM-compliant.

23. The system of claim 20, wherein the Server Proxy is further configured to separate a Digital Imaging Communications in Medicine (DICOM) header from image information prior to compression of the image information by the encoder.

24. The system of claim 20, wherein the encoder is further configured to compress the image data in accordance with a lossy compression scheme.

25. The system of claim 24, wherein the encoder is further configured to compress the image data in accordance with an H.264 compression standard.

* * * * *